(12) United States Patent
Sharei et al.

(10) Patent No.: US 10,124,336 B2
(45) Date of Patent: Nov. 13, 2018

(54) SELECTIVE DELIVERY OF MATERIAL TO CELLS

(71) Applicant: Massachusetts Institute of Technology, Cambridge, MA (US)

(72) Inventors: Armon R. Sharei, Watertown, MA (US); Viktor A. Adalsteinsson, Kennett Square, PA (US); Nahyun Cho, Closter, NJ (US); Robert S. Langer, Newton, MA (US); J. Christopher Love, Somerville, MA (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/912,001

(22) PCT Filed: Aug. 15, 2014

(86) PCT No.: PCT/US2014/051343
§ 371 (c)(1),
(2) Date: Feb. 12, 2016

(87) PCT Pub. No.: WO2015/023982
PCT Pub. Date: Feb. 19, 2015

(65) Prior Publication Data
US 2016/0193605 A1 Jul. 7, 2016

Related U.S. Application Data

(63) Continuation of application No. 61/866,972, filed on Aug. 16, 2013.

(51) Int. Cl.
*B01L 3/00* (2006.01)
*C12N 5/09* (2010.01)
(Continued)

(52) U.S. Cl.
CPC ...... *B01L 3/502761* (2013.01); *C12N 5/0634* (2013.01); *C12N 5/0693* (2013.01);
(Continued)

(58) Field of Classification Search
CPC ............ G01N 15/1459; G01N 33/574; G01N 15/1484; G01N 1/30; G01N 2015/1006;
(Continued)

(56) References Cited

U.S. PATENT DOCUMENTS 4,055,799 A 10/1977 Coster
4,835,457 A 5/1989 Hanss
(Continued)

FOREIGN PATENT DOCUMENTS

EP 0882448 B1 12/1998
EP 1 225 228 A2 7/2002
(Continued)

OTHER PUBLICATIONS

Chaw et al. Multi-step microfluidic device for studying cancer metastasis. Lab on a Chip (2007), v7, p. 1041-1047.*
(Continued)

*Primary Examiner* — Sean C. Barron
(74) *Attorney, Agent, or Firm* — Wolf, Greenfield & Sacks, P.C.

(57) ABSTRACT

Isolating or identifying a cell based on a physical property of said cell can include providing a cell suspension; passing said suspension through a microfluidic channel that includes a constriction; passing the cell suspension through the constriction; and, contacting said cell suspension solution with a compound. The constriction can be sized to preferentially deform a relatively larger cell compared to a relatively smaller cell.

19 Claims, 8 Drawing Sheets

(51) Int. Cl.

| | | |
|---|---|---|
| C12N 5/078 | (2010.01) | |
| G01N 15/14 | (2006.01) | |
| C12Q 1/04 | (2006.01) | |
| G01N 33/574 | (2006.01) | |
| G01N 15/00 | (2006.01) | |
| B82Y 30/00 | (2011.01) | |
| G01N 1/30 | (2006.01) | |
| G01N 15/10 | (2006.01) | |

(52) U.S. Cl.
CPC ............ *C12Q 1/04* (2013.01); *G01N 15/1459* (2013.01); *G01N 15/1484* (2013.01); *G01N 33/574* (2013.01); *B01L 2200/0652* (2013.01); *B01L 2300/08* (2013.01); *B01L 2400/0487* (2013.01); *B82Y 30/00* (2013.01); *G01N 1/30* (2013.01); *G01N 2015/0065* (2013.01); *G01N 2015/1006* (2013.01); *G01N 2015/1081* (2013.01)

(58) Field of Classification Search
CPC ... G01N 2015/0065; G01N 2015/1081; C12Q 1/04; B01L 3/502761; B01L 2300/08; B01L 2200/0652; B01L 2400/0487; B82Y 30/00; C12N 5/0693; C12N 5/0634
See application file for complete search history.

(56) References Cited

U.S. PATENT DOCUMENTS

| | | |
|---|---|---|
| 5,023,054 A | 6/1991 | Sato |
| 5,643,577 A | 7/1997 | Pang et al. |
| 5,658,892 A | 8/1997 | Flotte |
| 5,842,787 A | 12/1998 | Kopf-Sill |
| 5,951,976 A | 9/1999 | Segal |
| 6,156,181 A | 12/2000 | Parce |
| 6,186,660 B1 | 2/2001 | Kopf-Sill |
| 6,218,166 B1 | 4/2001 | Ravindranath et al. |
| 6,410,329 B1 | 6/2002 | Hansen et al. |
| 6,461,867 B1 | 10/2002 | Cai et al. |
| 6,562,616 B1 | 5/2003 | Toner |
| 7,109,034 B2 | 9/2006 | Orwar et al. |
| 7,704,743 B2 | 4/2010 | Fedorov et al. |
| 7,993,821 B2 | 8/2011 | Chiu |
| 8,211,656 B2 | 7/2012 | Hyde et al. |
| 8,669,044 B2 | 3/2014 | Chiu |
| 8,844,570 B2 | 9/2014 | Glick et al. |
| 9,005,579 B2 | 4/2015 | Nowinski et al. |
| 9,017,991 B2 | 4/2015 | Diefenbach |
| 9,157,550 B2 | 10/2015 | Wheeler |
| 9,255,245 B2 | 2/2016 | Bernick et al. |
| 2003/0133922 A1 | 7/2003 | Kasha, Jr. |
| 2004/0176282 A1 | 9/2004 | Dalby et al. |
| 2004/0197898 A1 | 10/2004 | Nakatani |
| 2005/0026283 A1 | 3/2005 | Ormar et al. |
| 2006/0134067 A1 | 6/2006 | Liu et al. |
| 2006/0134772 A1 | 6/2006 | Miles et al. |
| 2006/0223185 A1 | 10/2006 | Fedorov |
| 2007/0243523 A1 | 10/2007 | Ionescu-Zanetti et al. |
| 2007/0249038 A1 | 10/2007 | Adamo et al. |
| 2008/0311140 A1 | 12/2008 | Lee et al. |
| 2008/0318324 A1 | 12/2008 | Chiu et al. |
| 2009/0209039 A1 | 9/2009 | Adamo |
| 2009/0280518 A1 | 11/2009 | Adamo et al. |
| 2010/0203068 A1 | 8/2010 | Betz et al. |
| 2010/0249621 A1 | 9/2010 | Ichitani |
| 2010/0323388 A1 | 12/2010 | Chiu et al. |
| 2011/0030808 A1 | 2/2011 | Chiou et al. |
| 2011/0091973 A1 | 4/2011 | Glaser et al. |
| 2011/0300205 A1 | 12/2011 | Geall et al. |
| 2012/0107925 A1 | 5/2012 | Li et al. |
| 2012/0207745 A1 | 8/2012 | Godfrin et al. |
| 2013/0023051 A1 | 1/2013 | Bundock et al. |
| 2013/0045211 A1 | 2/2013 | Nowinski |
| 2013/0065314 A1 | 3/2013 | MacMillan |
| 2014/0011226 A1 | 1/2014 | Bernick |
| 2014/0273229 A1 | 9/2014 | Meacham et al. |
| 2014/0287509 A1 | 9/2014 | Sharei et al. |
| 2015/0184127 A1 | 7/2015 | White et al. |
| 2015/0196913 A1 | 7/2015 | Liu |
| 2016/0017340 A1 | 1/2016 | Wu |
| 2016/0199837 A1 | 7/2016 | Breinlinger |
| 2017/0020926 A1 | 1/2017 | Mata-Fink et al. |
| 2017/0326213 A1 | 11/2017 | Jajosky et al. |
| 2018/0003696 A1 | 1/2018 | Sharei et al. |
| 2018/0016539 A1 | 1/2018 | Ding et al. |
| 2018/0085402 A1 | 3/2018 | Kahvejian et al. |
| 2018/0142198 A1 | 5/2018 | Sharei et al. |

FOREIGN PATENT DOCUMENTS

| | | |
|---|---|---|
| EP | 2169070 | 3/2010 |
| JP | H01196566 | 8/1989 |
| JP | H03257366 | 11/1991 |
| JP | 2010-025852 A | 2/2010 |
| JP | 2011-163830 A | 8/2011 |
| WO | WO 1985/000748 A1 | 2/1985 |
| WO | WO 1997/020570 A1 | 6/1997 |
| WO | WO 02/067863 A2 | 9/2002 |
| WO | WO 03/020039 A1 | 3/2003 |
| WO | WO 2004/001424 A1 | 12/2003 |
| WO | WO 2006/010521 A2 | 10/2006 |
| WO | WO 2006/105251 A2 | 10/2006 |
| WO | WO 2007/097934 A2 | 8/2007 |
| WO | WO 2008/0214565 A2 | 2/2008 |
| WO | WO 2009/056332 A1 | 5/2009 |
| WO | WO 2010/016800 A1 | 2/2010 |
| WO | WO 2010/077290 A1 | 7/2010 |
| WO | WO 201 0/1 051 3 | 9/2010 |
| WO | WO 2010/129671 A3 | 11/2010 |
| WO | WO 2010/145849 A2 | 12/2010 |
| WO | WO 2011/051346 A1 | 5/2011 |
| WO | WO2011/119492 | 9/2011 |
| WO | WO 2012/097450 A1 | 7/2012 |
| WO | WO 2012/106536 A2 | 8/2012 |
| WO | WO 2012/118799 | 9/2012 |
| WO | WO 2012/162779 A1 | 12/2012 |
| WO | WO 2013/059343 A1 | 4/2013 |
| WO | WO 2014/165707 A2 | 10/2014 |
| WO | WO 2015/023982 A1 | 2/2015 |
| WO | WO 2015/061458 | 4/2015 |
| WO | WO 2015/153102 A1 | 10/2015 |
| WO | WO 2016/003485 A1 | 1/2016 |
| WO | WO 2016/070136 A1 | 5/2016 |
| WO | WO 2016/077761 A1 | 5/2016 |
| WO | WO 2016/109864 | 7/2016 |
| WO | WO 2016/115179 | 7/2016 |
| WO | WO 2016/183482 A1 | 11/2016 |
| WO | WO 2017/008063 A1 | 1/2017 |
| WO | WO 2017/041050 A1 | 3/2017 |
| WO | WO 2017/041051 A1 | 3/2017 |
| WO | WO 2017/106899 A2 | 6/2017 |
| WO | WO 2017/123644 A1 | 7/2017 |
| WO | WO 2017/123646 A1 | 7/2017 |

OTHER PUBLICATIONS

Swaminathan et al. Mechanical Stiffness Grades Metastatic Potential in Patient Tumor Cells and in Cancer Cell Lines. Cancer Research (2011), v71(15), p. 5075-5080.*

Hosokawa et al. Size-Selective Microcavity Array for Rapid and Efficient Detection of Circulating Tumor Cells. Anal. Chem. (2010), v82, p. 6629-6635.*

Cancer Facts & Figures 2012. Published by the American Cancer Society in Atlanta, 68 pages.*

Janeway Jr et al. Immunobiology: The Immune System in Health and Disease. 5th edition (2001), Chapter "The structure of a typical antibody molecule", NCBI Bookshelf NBK27144, 5 page reprint.*

BD Bioscience FITC-labeled anti-CD45 antibody.*

BD Bioscience PE-labeled anti-EpCAM antibody.*

(56) References Cited

OTHER PUBLICATIONS

Boohaker et al. The Use of Therapeutic Peptides to Target and to Kill Cancer Cells. Curr Med Chem. (2012); 19(22), 26 page reprint.*
Hoskin et al. Studies on anticancer activities of antimicrobial peptides. Biochimica et Biophyscia Acta (2008), v1778, p. 357-375.*
Gasteiger et al. The Proteomics Handbook (2005), Chapter 52, pp. 571-607.*
Hoeppener A.E.L.M., Swennenhuis J.F., Terstappen L.W.M.M. (2012) Immunomagnetic Separation Technologies. In: Ignatiadis M., Sotiriou C., Pantel K. (eds) Minimal Residual Disease and Circulating Tumor Cells in Breast Cancer. Recent Results in Cancer Research, vol. 195. Springer, Berlin, Heidelberg.*
Adamo, Andrea et al., "Microfluidics-Based Assessment of Cell Deformability," *Analytical Chemistry* (Aug. 7, 2012), vol. 84, No. 15, pp. 6438-6443.
Augustsson et al. "Microfluidic, Label-Free Enrichment of Prostate Cancer Cells in Blood Based on Acoustophoresis," *Analytical Chemistry*, Aug. 28, 2012 (Aug. 28, 2012), vol. 84, No. 18, pp. 7954-7962.
Cross et al., "Nanomechanical analysis of cells from cancer patients," *Nature Nanotechnology* (Dec. 2007), vol. 2, pp. 780-783.
European Search Opinion dated Apr. 30, 2015 from European Application No. 12 841 329, 2 pp.
Griesbeck et al., "Sex Differences in Plasmacytoid Dendritic Cell Levels of IRF5 Drive higher IFN-alpha production in Women," *The Journal of Immunology* (Dec. 2015), vol. 195(11):5327-5336.
Hallow et al., "Shear-Induced Intracellular Loading of Cells With Molecules by Controlled Microfluidics," *Biotechnology and Bioengineering* (2008), vol. 99(4):846-854.
Han, X. et al., "CRISPR-Cas9 delivery to hard-to-transfect cells via membrane deformation," *Sci. Adv.*, Aug. 14, 2015, e1500454, 8 pp.
Hillerdal et al., "Systemic treatment with CAR-engineered T cells against PSCA delays subcutaneous tumor growth and prolongs survival of mice," *BMC Cancer* (Jan. 18, 2014), vol. 14, No. 30, pp. 1-9.
International Preliminary Report on Patentability dated Feb. 16, 2016 from International Application No. PCT/US2014/051343.
International Search Report and Written Opinion dated Feb. 1, 2016 from International Application No. PCT/US15/60689.
International Search Report and Written Opinion dated Mar. 11, 2016 from International Application No. PCT/US15/584489.
International Search Report and Written Opinion dated Mar. 21, 2016 from International Application No. PCT/US2016/013113.
International Search Report and Written Opinion dated Dec. 18, 2014 from International Application No. PCT/US2014/051343.
Lee et al., "Nonendocytic delivery of functional engineered nanoparticles into the cytoplasm of live cells using a novel, high-throughput microfluidic device," Nano Letters (2012), vol. 12, pp. 6322-6327.
Lin et al., "Highly selective biomechanical separation of cancer cells from leukocytes using microfluidic and hydrodynamic concentrator," Biomicrofluidics (Jun. 26, 2013), vol. 7, No. 3, pp. 34114-1-11.
Liu et al., "Molecular imaging in tracking tumor-specific cytotoxic T lymphocytes (CTLs)," Theranostics (Jul. 28, 2014), vol. 4, No. 10, pp. 990-1001.
Liu et al., "Spatially selective reagent delivery into cancer cells using a two-layer microfluidic culture system," *Analytica Chimica Acta* (Sep. 1, 2012), vol. 743, pp. 125-130.
Office Action dated May 13, 2016 from Chinese Application No. 201280060689.6, 4 pp.
Office Action dated Jun. 14, 2016 from European Application No. 12 841 329, 4 pp.
Sharei et al, "Ex vivo Cytosolic Delivery of Functional Macromolecules to Immune Cells," (Apr. 13, 2015), PLoS One, vol. 10, No. 4, 12 pp. e0118803.
Sharei et al., "A vector-free microfluidic platform for intracellular delivery," *Proc. Natl. Acad. Sci. USA* (Feb. 5, 2013), vol. 110, No. 6, pp. 2082-2087.

Sharei et al., "Cell Squeezing as a Robust, Microfluidic Intracellular Delivery Platform," Journal of Visualized Experiments (Nov. 7, 2013), No. 81, 9 pp.
Sharei et al., "Microfluidic Cell Deformation As a Robust, Vector-Free Method for Cystosolic Delivery of Macromolecules 2012 Annual Meeting," (Jan. 1, 2012), 3 pp.
Sharei et al., "Plasma membrane recovery kinetics of a microfluidic intracellular delivery platform," Integrative Biology (2014), vol. 6, pp. 470-475.
Shelby et al., "A microfluidic model for single-cell capillary obstruction by Plasmodium falciparum infected erythrocytes," (Dec. 9, 2003), *Proc. Nat. Acad. Sci.*, vol. 100, No. 25, pp. 14618-14622.
Supplementary European Search Report dated Apr. 30, 2015 from European Application No. 12 841 329, 3 pp.
Third-Party Submission mailed Oct. 23, 2015 from U.S. Appl. No. 14/352,354, 21 pp.
Zarnitsyn et al., "Electrosonic ejector microarray for drug and gene delivery," Biomed Microdevices (2008) 10:299-308.
International Search Report and Written Opinion dated Feb. 25, 2013 from International Application No. PCT/US12/060646.
Office Action dated Jul. 7, 2016 from Japanese Application No. 2014-537184, 7 pp.
Downs, C. A. et al. (May 14, 2011). "Cell Culture Models Using Rat Primary Alveolar type 1 Cells", Pulmonary Pharm. & Therapeutics 24(5)577-586.
Extended European Search Report for EP 14836593.5, dated Feb. 23, 2017, 9 pages.
Howarth, M. et al. (May 2008). "Monovalent, Reduced-Size Quantum Dots For Imaging Receptors On Living Cells," Nature Methods 5(5):397-399.
International Preliminary Report on Pattentability, PCT/US2012/060646, dated Apr. 22, 2014, 7 pages.
International Preliminary Report on Pattentability, PCT/US2015/058489, dated May 2, 2017, 12 pages.
International Preliminary Report on Pattentability, PCT/US2015/060689, dated May 16, 2017, 10 pages.
Kim, D., et al., "Microengineered Platforms for Cell Mechanobiology," Annual Review of Biomedical Engineering, 2009, vol. 11, pp. 203-233.
Liu, W. et al. (Jan. 20, 2010). "Compact Biocompatible Quantum Dots Via RAFT-Mediated Synthesis of Imidazole-Based Random Copolymer Ligand," JACS 132(2):472-483.
Matthews, B.D., et al., "Cellular adaptation to mechanical stress: role of integrins, Rho, cytoskeletal tension and mechanosensitive ion channels," Journal of Cell Science, vol. 119, pp. 508-518, 2006.
Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.
Sharei, A. et al., "Plasma membrane recovery kinetics of a microfluidic intracellular delivery platform," Integr Biol (Apr. 1, 2014) 6(4):470-475.
Williams, A.R. et al. (Nov. 5, 1999). "Filtroporation: A Simple, Reliable Technique for Transfection and Macromolecular Loading of Cells", Biotechnology and Bioengineering 65(3)341-346.
U.S. Appl. No. 15/523,142, filed Apr. 28, 2017, Sharei et al.
U.S. Appl. No. 15/526,517, filed May 12, 2017, Peng et al.
U.S. Appl. No. 15/542,892, filed Jul. 11, 2017, Sharei et al.
ATCC Thawing, Propagating, and Cryopreserving Protocol, NCI-PBCF-HTB81 (DU 145), Prostate Carcinoma (ATCC® htb-81), Version 1.6, 2012, 23 pages.
Examination Report No. 1 dated Dec. 1, 2016 from Australian Application No. 2012326203, 10 pages.
Examination Report No. 2 dated Jul. 26, 2017 from Australian Application No. 2012326203, 6 pages.
Office Action dated Dec. 17, 2014 from Chinese Office Action No. 201280060689.6, 9 pages.
Office Action dated Sep. 6, 2015 from Chinese Office Action No. 201280060689.6, 8 pages.
Office Action dated Dec. 1, 2016 from Chinese Application No. 201280060689.6, 4 pages.
Office Action dated Jun. 23, 2017 from Chinese Application No. 201280060689.6, 4 pages.

(56) References Cited

OTHER PUBLICATIONS

Office Action dated Oct. 11, 2017 from European Application No. 12 841 329, 4 pages.
Office Action dated Jul. 27, 2016 from U.S. Appl. No. 14/352,354, 9 pages.
Office Action dated Feb. 24, 2017 from U.S. Appl. No. 14/352,354, 11 pages.
Office Action dated Oct. 26, 2016 from Russian Application No. 2014119926/10(031699), 10 pages.
Office Action dated Mar. 23, 2017 from Russian Application No. 201411926/10(031699), 10 pages.
Office Action dated Jul. 7, 2016 from Japanese Application No. 2014-537184, 14 pages.
Office Action dated May 1, 2017 from Japanese Application No. 2014-537184, 13 pages.
Office Action dated Jul. 5, 2017 from Chinese Application No. 201480056295.2, 13 pages.
Banz, A. et al., "Tumor Growth Control Using Red Blood Cells as the Antigen Delivery System and Poly(I:C)," J Immunother 2012, 35(5), pp. 409-417.
Certificate of Grant dated Jan. 11, 2018 for Chinese Application No. 201280060689.6.
Cremel, L. et al., "Innovative approach in Pompe disease therapy: Induction of immune tolerance by antigen-encapsulated red blood cells," Int J Pharm. Aug. 1, 2015;491(1-2), pp. 69-77.
Cremel, L. et al., "Red blood cells as innovative antigen carrier to induce specific immune tolerance," Int J Pharm. Feb. 25, 2013;443(1-2), pp. 39-49.
Ding, X. et al., "High-throughput nuclear delivery and rapid expression of DNA via mechanical and electrical cell-membrane disruption," Nature Biomedical Engineering (2017), vol. 1, No. 3, 7 pages.
Eixarch, H. et al. "Tolerance induction in experimental autoimmune encephalomyelitis using non-myeloablative hematopoietic gene therapy with autoantigen." Molecular Therapy 17.5 (2009): 897-905.
Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).
Examination Report No. 1 dated Apr. 19, 2018 from Australian Application No. 2014306423, 4 pages.
Extended European Search Report for EP 16737769.6, dated May 3, 2018, 11 pages.
Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Grimm, A. J. et al., "Memory of tolerance and induction of regulatory T cells by erythrocyte-targeted antigens," Sci Rep. Oct. 29, 2015;5:15907, 11 pages.
Hao, Y. et al., "Delivery technologies for genome editing," Nature Reviews (2017), vol. 16, No. 6, pp. 387-399.
International Search Report and Written Opinion dated Jan. 12, 2016 from International Application No. PCT/US2016/050288, 14 pages.
International Search Report and Written Opinion dated Jan. 3, 2017 from International Application No. PCT/US2016/050287, 13 pages.
International Search Report and Written Opinion dated Sep. 19, 2017 from International Application No. PCT/US2017/030932, 18 pages.
International Search Report and Written Opinion dated Jul. 21, 2017 from International Application No. PCT/US2017/030933, 20 pages.
Li, J. et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Lorenz, K. M. et al., "Engineered binding to erythrocytes induces immunological tolerance to E. coli asparaginase," Sci Adv. Jul. 17, 2015;1(6):e1500112, 11 pages.
Mali, P. et al., "RNA-guided human Genome Engineering via Cas9," Science (2013), vol. 339, No. 6121, pp. 823-826.
Milo, R. "What is the total number of protein molecules per cell volume? A call to rethink some published values." Bioessays 35.12 (2013): 1050-1055.
Notice of Reasons for Rejection dated Jun. 4, 2018 from Japanese Application No. 2016-534877, 6 pages.
Office Action dated May 18, 2018 from U.S. Appl. No. 14/352,354, 9 pages.
Partial Supplementary European Search Report dated May 30, 2018 for European Application No. 15855640.7, 19 pages.
Partial Supplementary European Search Report dated Jun. 11, 2018 for European Application No. 15859824.3, 17 pages.
Restriction Requirement dated May 15, 2018 from U.S. Appl. No. 15/523,142, 12 pages.
Ravilla et al., "Erythrocytes as Carrier for Drugs, Enzymes and Peptides," Journal of Applied Pharmaceutical Science, vol. 2, No. 2, pp. 166-176 (2012).
Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).
Rossi, L. et al., "Erythrocyte-mediated delivery of phenylalanine ammonia lyase for the treatment of phenylketonuria in BTBR-Pah$^{enu2}$ mice," Journal of Controlled Release 194; 37-44 (2014).
Rughetti, A. et al., "Transfected human dendritic cells to induce antitumor immunity," Gene Therapy, vol. 7, pp. 1458-1466 (2000).
Rutella et al., "Tolerogenic dendritic cells: cytokine modulation comes of age," Blood, vol. 108, No. 5, pp. 1435-1440 (2006).
Steinman et al., "Tolerogenic dendritic cells," Annual Review of Immunology, vol. 21, pp. 685-711 (2003).
Stevenson, D. J. et al., "Single cell optical transfection," IEEE Transactions on Ultrasonics, Ferroelectrics and Frequency Control, vol. 53, No. 1, 117-871 (2010).
Stewart et al., "In vitro and ex vivo strategies for intracellular delivery," Nature, vol. 538, No. 7624, pp. 183-192 (2016).
Szeto et al., "Microfluidic squeezing for intracellular antigen loading in polyclonal B-cells as cellular vaccines," Scientific Reports, vol. 5, 10276 (May 2015), 13 pages.
Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).

* cited by examiner

Protocol

1. Lyse red blood cells

2. Deliver dye via CellSqueeze

3. Sort cells

PBMCs

HT-29

SK-MEL-5

PANC-1

SELECTIVE DELIVERY OF MATERIAL TO CELLS

CROSS-REFERENCE TO RELATED APPLICATIONS

This application is a national stage application, filed under 35 U.S.C. § 371, of International Application No. PCT/US2014/051343, filed on Aug. 15, 2014, which claims benefit of priority to U.S. Provisional Patent Application No. 61/866,972 filed Aug. 16, 2013, the entire contents of which is hereby expressly incorporated by reference.

GOVERNMENT SUPPORT

This invention was made with Government support under Grant Nos. R01 GM101420, P30 CA014051, and EB011187 awarded by the National Institutes of Health. The Government has certain rights in the invention.

TECHNICAL FIELD

The field of the invention relates to size-selective delivery of material to cells.

BACKGROUND

Intracellular delivery of materials is a challenge. Existing technologies that rely on nanoparticles, electrical fields, pore-forming chemicals, etc. are capable of delivering some materials to certain cell types but often in an indiscriminant fashion with regards to the physical properties of the target cell. By developing selective delivery methods dependent on the physical properties of the target cells, one could exert more robust control in delivery activity for research, diagnostic or therapeutic applications. For example, Circulating tumor cells (CTCs) are tumor cells found in the bloodstream, believed to mediate metastasis, or the spread of cancer, to distant sites in the body. Approximately 90% of human deaths from cancer are due to metastasis. Identification and characterization of CTCs could be the key to understanding, treating, or preventing metastatic cancer. Moreover these cells are known to have different physical properties compared to the surrounding blood cells.

SUMMARY

The current subject matter provides devices, systems, and methods for selectively delivering material to one or more cells based on their physical properties, such as size, volume, diameter, cytosol viscosity, or membrane stiffness. For example materials can be delivered in a cell size dependent manner. A cell suspension containing differentially sized cells can be run through a device in the presence of the target delivery material (e.g., a dye, a protein, nucleic acid, and the like) and these materials can be selectively delivered to the larger cells within the population. The mechanism of delivery in the data being through selective disruption of the cell membrane of larger cells as they are deformed in a channel constriction while smaller cells are not deformed enough to cause membrane disruption.

In some example implementations, labelling tumor cells relative to non-tumor cells can be achieved. Cells are run through a device for size selective tagging using fluorescent dyes or other detectable markers. The cells are optionally stained with an antibody, e.g., a tumor cell selective antibody, e.g., antibodies against CD45 to provide further contrast between cancer cells and blood cells (most blood cells are CD45+). The samples are run through a cell sorter, e.g. a standard fluorescence-activated cell sorter (FACS).

In some example implementations, labeling of cells based on their cell cycle can be achieved because cells within a population that are closer to division are larger than those that have just undergone division. Delivery of a dye to the bigger cells within a population can be used to identify the individual cells that are in a later stage of their cell cycle.

In some example implementations, therapeutics for blood cancers (e.g. lymphomas) can be achieved because lymphoma cells are often bigger than the surrounding blood cells thus an intracellular toxin can be delivered to lymphoma cells but not the healthy surrounding blood cells. This can induce selective death of diseased cells.

Tagged cells can be isolated by fluorescence or magnetic purification techniques. Flow cytometry or microarrays with robotic manipulators can be used to select cells based on fluorescence, while magnetic columns, microfluidic magnetic separation systems, or magnetic sweepers can be used to isolate magnetically tagged particles.

Cells can be identified based on relative size or diameter. Thus, relatively larger cells selectively or preferentially take up markers, because the extent of cell membrane disruption is relatively greater in larger cells, i.e., larger cells are deformed to a greater extent compared to smaller cells. Due to the greater degree of membrane disruption of larger cells, at least 10%, 25%, 50%, 2-fold, 5-fold, 10-fold, 100-fold or more of a payload molecule gains access to the inside (cytoplasm) of a larger cell compared to a smaller cell. As a result of the uptake of detectable markers in this manner and subsequent sorting based on uptake of the marker, the purity of tumor cells is enhanced by 100 times; 1,000 times, and up to 10,000 times or more compared to the level of purity in peripheral blood. Purity is assessed by an antibody that targets/binds to a known marker that is expressed/overexpressed by tumor cells. Alternatively, antibodies against markers that are not expressed by tumor cells but are expressed/overexpressed by blood cells (CD45 is an example). Either approach helps provide increased contrast to sort out the cells of interest.

Samples with high size-tag fluorescence and low CD45 fluorescence are captured as candidate/potential CTCs. FACS outputs are inherently relative. A "high" signal is minimum one decade (ten times higher level) of fluorescence intensity above the baseline control signal, and a "low" is one decade below the positive control population.

The device and methods of the invention provide a solution to the long-standing problem of how to identify and/or isolate approximately for more (2, 5, 10, 100, 1,000 or more) CTCs per 1-10 million leukocytes in a patient-derived sample of blood. For example, 1 CTC per ml of blood is clinically relevant in a cancer patient. Accordingly, a method for isolating or identifying a circulating tumor cell comprises the steps of providing a cell suspension; passing the solution through a microfluidic channel that includes a constriction, the constriction being sized to preferentially deform a circulating tumor cell compared to a leukocyte; passing the cell suspension through the constriction; and contacting the cell suspension solution with a detectable marker. The suspension can be passed through a microfluidic channel that includes a constriction, the constriction being sized to preferentially deliver a compound to a group of cells having a relatively different physical property than another group of cells. The physical property can include cell size, diameter, cytosol viscosity, and/or membrane stiffness (e.g., as measured by transit time assays, stiffer cells pass through specialized microchannels more slowly than less stiff cells, e.g., as described in Sharei et al., 2012, Anal. Chem. 84(15):6438-6443; Cross et al., 2007, Nature Nanotechnology 2:780-783). The contact can happen after deformation treatment. Or the material can be premixed with the cells before deformation treatment. Both CTCs and leukocytes are deformed; however larger cells are deformed to a greater degree and therefore, molecules are selectively delivered to such cells, thereby treating or tagging them.

For example, the marker comprises a detectably labeled, e.g., fluorescently or magnetically labeled material, such as a dye or particle. The dyes or particles need not be tumor specific. Optionally, they differentially bind to tumor cells (e.g., at least 20%, 50%, 2 times, 5 times, or more compared to non-tumor cells). However, the specificity of the method is based on the discovery that tumor cells are slightly larger than leukocytes and the device is highly size selective. This size difference depends on the tumor type. For example, tumor cells are generally from 50%-400% larger than the leukocytes. Therefore, the delivery material preferentially enters into cells that are large enough to be tagged via size-specific deformation of cells. The delivered tag is then in turn detected to identify the CTC.

In one example, the suspension comprises whole blood. Alternatively, the cell suspension is a mixture of cells in a physiological saline solution other than blood. Typically, the cell suspension comprises whole blood of a subject at risk of or diagnosed as comprising a tumor. For example, the patient is suspected of having, has been diagnosed as having, or is suspected or diagnosed as having metastatic disease of melanoma, colon, prostate, breast, liver, lung, pancreatic, brain, or blood. CTCs can be present before the patient has developed metastatic disease. Therefore, early detection of CTCs is clinically important, because such detection represents an early identification of patients likely to progress to develop metastatic disease.

Optionally, erythrocyte lysis is carried out as a pretreatment step prior to flowing cells through the device.

The device is characterized by physical parameters that distinguish tumor cells from non-tumor cells, e.g., normal erythrocytes or leukocytes. For example, the constriction comprises a width from 4 µm-10 µm, length of 1 µm-100 µm, and 1-10 constrictions in series. The estimated speed of the cells can range from 10 mm/s to 10 m/s. To push or propel the cell suspension through the device, the method further comprises applying a pressure to cells. Pressure is used to drive the cell suspension through the device, and the transit through the constriction point is what deforms the cells and leads to membrane disruption, and therefore delivery.

The method involves introducing into the tumor cell a detectable compound. Thus, the cell suspension comprises a payload or the method further comprises a step of incubating said cell suspension in the solution containing a payload for a predetermined time after it passes through the constriction. For example, the payload comprises a magnetic particle such as a nanoparticle, a fluorescent particle, such as a quantum dot or carbon nanotube, or a fluorescent dye or protein, or genetic material (DNA or RNA) that codes for a fluorescent protein or other compound that enables detection (e.g., luciferase). Alternatively one could deliver a combination of the aforementioned materials to enable detection and simultaneous manipulation of the cells. For example, one could deliver a fluorescent particle to enable sorting and co-deliver DNA, RNA or a protein to facilitate subsequent tumor cell survival and encourage its growth and proliferation post-sorting to enable further studies of cultured metastatic cells.

Also within the invention is a microfluidic system for distinguishing tumor cells from non-tumor cells, comprising a microfluidic channel defining a lumen and being configured such that a tumor cell suspended in a buffer can pass therethrough and is constricted compared to a non-tumor cell. Non tumor cells may be deformed to some extent; however, the key is that the tumor cells are deformed enough to cause a cell membrane disruption whereas the non-tumor cells are not deformed enough to result in membrane disruption due to their smaller relative size. The membranes of smaller cells are not disrupted or disrupted less than larger cells, e.g., in some cases, both smaller and larger cells are disrupted but smaller cells receive less material than the larger cells. The microfluidic channel includes a cell-deforming constriction, wherein a diameter of the constriction is a function of the diameter of the cell. The constriction is sized to preferentially deform a tumor cell compared to a non-tumor cell. This preferential deformation is designed to selectively facilitate the delivery of the target material to tumor cells vs. non tumor cells. Selective delivery enables one to enrich the desired tumor population through sorting/enrichment methods such as flow cytometery (FACS), micromanipulation, magnetic separation, cell culture.

The method is carried out at physiological temperature, e.g., 37° C., room temperature, e.g., 20° C., or alternatively, at 0-4° C. In some cases, the latter is preferred, because it can yield better delivery performance due to delayed membrane repair and minimize background from endocytosis by reducing the endocytotic activity of cells. As described above, the cell suspension is whole blood or any mammalian cell suspension in a physiological buffer solution such as phosphate buffers saline (PBS) or tissue culture media as a delivery buffer. In some examples, PBS is preferred due to reduced effects from Ca or Mg in tissue culture media.

In an aspect, isolating or identifying a cell based on a physical property of the cell can include providing a cell suspension; passing the suspension through a microfluidic channel that includes a constriction; passing the cell suspension through the constriction; and, contacting the cell suspension solution with a compound. The constriction can be sized to preferentially deform a relatively larger cell compared to a relatively smaller cell.

In another aspect, a microfluidic system for distinguishing tumor cells from non-tumor cells can include a microfluidic channel defining a lumen and being configured such that a tumor cell suspended in a buffer can pass therethrough and is constricted compared to a non-tumor cell. The microfluidic channel can include a cell-deforming constriction. A diameter of the constriction can be a function of the diameter of the cell.

One or more of the following features can be included. For example, the physical property can be one or more of size and diameter. The cell suspension can include one or more of: peripheral blood cells; and at least two different cell types having different physical properties. The cell suspension can include an erythrocyte-depleted population of peripheral blood cells. The larger cell can include a circulating tumor cell and the smaller cell can include a leukocyte. The compound can include a molecular mass of 0.5 kDa to 5 MDa. The compound can include a molecular mass of 3 kDa to 10 kDa. The compound can include a detectable marker (e.g., quantum dots, cyanine, fluorescein, rhodamine, and derivatives thereof such as fluorescein isothiocyanate (FITC) or Tetramethylrhodamine isothiocyanate (TRITC) or NHS-Rhodamine, maleimide activated fluorophores such as fluorescein-5-maleimide, as well as Alexa Fluors), an active biomolecule, and/or a toxin, (e.g., Pseudomonas exotoxin, Diphtheria toxin, and ricin, caspase proteins, antibodies that interfere with essential cell functions (e.g. antibodies against tubulin)) for selectively killing target cells. The compound can influence cell function (e.g. transcription factors, siRNA, DNA, mRNA, antibodies, small molecule drugs) and/or can induce cell death. The compound can enter the cell after the cell has passed through the constriction. The suspension can include whole blood. The suspension can include whole blood of a subject at risk of or diagnosed as comprising a tumor. The tumor can include melanoma, colon, prostate, lung, pancreatic, breast, liver, brain, or blood cancer. The constriction can include a width from 4 µm-10 µm, length of 1 µm-100 µm, and 1-10 constrictions in series. A speed of the cells traversing a constriction can range from 10 mm/s to 10 m/s. A pressure can be applied to the cell suspension to drive cells through the constriction of a microfluidic channel.

The cell suspension can include a payload or the cell suspension can be incubated in the solution containing a payload for a predetermined time after it passes through the constriction. The payload can include a magnetic particle a fluorescent particle, such as a quantum dot or carbon nanotube, or a fluorescent dye or protein, or genetic material (DNA or RNA) that codes for a fluorescent protein or other compound that enables detection (e.g. luciferase).The constriction can be sized to preferentially deform a tumor cell more than a non-tumor cell.

These and other capabilities of the invention, along with the invention itself, will be more fully understood after a review of the following figures, detailed description, and claims.

DETAILED DESCRIPTION

CTCs are tumor cells that are found in the bloodstream, and are believed to be responsible for the dissemination of cancer to distant organs. CTCs are regarded as minimally-invasive, "liquid biopsies" for cancer patients and are useful as prognostic indicators for patient outcome and treatment efficacy. Comprehensive characterizations of these single cells provide a better understanding of metastatic dissemination, treatment resistance, and tumor biology.

Figure 1:
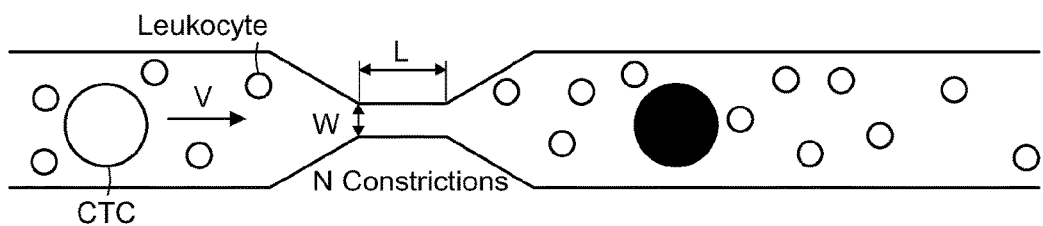
FIG. 1 is a diagram of a system for size selective tagging of CTCs by rapid mechanical deformation.

A typical human erythrocyte has a disk diameter of approximately 6.2-8.2 µm and a thickness at the thickest point of 2-2.5 µm and a minimum thickness in the center of 0.8-1 µm, being much smaller than most other human cells. Leukocytes (white blood cells) include neutrophils (12-14 µm diameter), eosinophils (12-17 µm diameter), basophils (14-16 µm diameter), lymphocytes (average 6-9 µm in diameter for resting, and 10-14 µm diameter for activated), and monocytes, the largest type of white blood cells that can be up to 20 µm in diameter. As shown in FIG. 1, the size difference between CTCs and hematologic cells generally permits distinguishing CTCs from other cells in circulating blood (CTCs ·9-20 µm; RBC ~8 µm discoid; leukocytes ~7-12 µm). See FIG. 1. Subsequent tumor cell specific labeling using antibodies (or cell-specific fragments thereof) or other tumor cell specific ligands increase the selectivity of the method.

Since CTCs are present as one in $10^6$-$10^7$ mononuclear cells in the bloodstream, high-sensitivity enrichment techniques are used that rely on immunological or morphological differences in CTCs from the blood cells. Immunological approaches often target epithelial cell surface markers (such as EpCAM) and tumor-specific proteins (such as Her2-neu, MUC1/MUC2, carcinoembryonic antigen (CEA), mammaglobulin, and alpha-fetoprotein) or aim to deplete CD45+ cells. Microfilters, density-gradient separations, and microfluidics platforms are examples of morphology-based methods. All of these approaches have inherent biases, suffer from low enrichment efficiencies and a significant number of CTCs may down-regulate surface antigens or exhibit varying morphological features. These biases pose a significant challenge in the field as it is still largely unknown which subset of CTCs are responsible for metastasis or are reliable prognostic markers. Thus, it is important to develop techniques that can ensure high sensitivity isolation of all candidate CTC sub-types to screen for the most clinically relevant candidates. The devices and methods described herein permit the isolation and enumeration of the CTC subtype of interest.

A combined enrichment method integrates both immunological and morphologic-based approaches to tag and isolate pure CTCs with less bias and based on tunable parameters. The method combines microfluidic intracellular delivery (FIG. 1) and antibody staining to yield robust, high sensitivity purification of circulating tumor cells from whole blood (FIG. 2) comprises a width from 4 μ-10 μm, length of 1 μm-100 μm, and 1-10 constrictions in series. The estimated speed of the cells can range from 10 mm/s to 10 m/s. The specific device parameters chosen are dictated by the target tumor cell type, e.g., a different device design is used to select CTCs for a melanoma patient vs. a colon cancer patient. Examples of tumor cell sizes/diameters include; melanoma ~15 um, colon cancer ~11 um, and pancreatic cancer ~15 um.

In this approach, a rapid mechanical deformation delivery system exploits the inherent size difference between many CTCs and the surrounding blood cells to selectively deliver fluorescent, magnetic and/or other distinguishing materials to the tumor cells. In further processing, antibody-based fluorescent and/or magnetic tagging is used to enhance the contrast between the candidate CTCs and the surrounding blood cells. By uniquely combining size-based and immunological approaches to CTC isolation, this technology has demonstrated utility for the non-biased isolation of candidate tumor cells from patient samples for analysis. In some implementations, both smaller and larger cells are deformed but the smaller cells membrane is not deformed to the point that the membrane becomes compromised. For example, to selectively delivering to 15 μm tumor cells in whole blood where most healthy white blood cells are ~8 μm in size, a 6 um width constriction can be used. Such a constriction would deform both cell types but would very preferentially disrupt the membrane of the 15 μm tumor cells not the 8 μm blood cells.

Clinical/Translation Relevance

CTCs are being explored as surrogates for tumor biopsies for understanding mechanisms of resistance and guiding the selection of targeted therapies. Measures of the number and composition of CTCs before and after treatment indicate treatment efficacy and prognosis. The approach utilizes a robust, high-throughput, disposable device for the tagging of CTCs based on cell size and surface antigens. Moreover, the ability to deliver a diversity of macromolecules also enables one to deliver molecular probes (such as antibodies, quantum dots, carbon nanotubes, and molecular beacons) that respond to the intracellular environment and thus provide further information on the intracellular properties of the target cell. This combinatorial approach provides a robust platform capable of enriching CTC populations that would have been missed by alternative methods that rely solely on immunological or morphological separation. The technique is useful to isolate patients' CTCs.

EXAMPLE 1

Whole blood or other cell suspensions are processed using both unlabeled and/or antibody-coated magnetic beads. These cells are then isolated using a high-fidelity, magnetic enrichment system for rare cells. A nanowell technology may also be used to achieve high purity isolations by imaging and robotically-retrieving single cells of interest from an elastomeric array of 84,672 subnanoliter wells.

Obtaining single, live, pure, intact CTCs of diverse phenotypes allows a host of characterization efforts from the genomic to functional levels with immediate clinical and translational relevance. The methods permit a highly sensitive and specific enrichment of live, diverse CTCs with reduced bias.

EXAMPLE 2

Magnetic nanoparticles are delivered to tumor cell lines & PBMCs. Nanoparticle delivery to EpCAM-expressing, epithelial cancer cell lines, e.g., HT-29, LNCaP, and SK-BR-3, is compared to bulk peripheral blood mononuclear cell (PBMC) suspensions derived from human blood.

10 nm iron-oxide nanoparticles with a polyethylene glycol (PEG) surface coating are delivered to cancer cells mixed with whole blood, and the resulting mixture of tagged cells are processed using the cell separation system described above. For example, the microfluidic delivery system was used to induce a rapid mechanical deformation of a cell to generate transient pores in the cell membrane (FIG. 1). The approach has demonstrated an ability to deliver a range of materials, including proteins, RNA, DNA and nanoparticles to a variety of cell types and works with whole blood, a medium that often poses problems for microfluidic systems.

Exemplary tagging molecules, e.g., 3 kDa and 70 kDa, fluorescently-labeled, dextran polymers as model molecules, were used to discriminate between PBMCs and two different cancer cell lines based on size alone. The results also indicate the utility of the system for the selective delivery of magnetic particles to tumor cells in the blood. PEG coated iron-oxide particles are used to magnetically tag colon cancer (e.g., as exemplified by the cell line HT-29). Further enrichment is accomplished using conjugation of FITC to the iron-oxide nanoparticle surface to directly measure nanoparticle uptake.

PEG coated 10 nm iron-oxide nanoparticles are delivered to cell suspensions that are suspected of containing or are known to contain CTCs, e.g., a patient-derived blood sample, or cell lines HT-29, LNCaP, and SK-BR-3 cells, separately mixed with whole blood. The resulting mixture of tagged cells are then purified, e.g., using a high fidelity magnetic separator. The separator accurately discriminates between the model CTCs with high iron-oxide content and less- effectively labeled PBMCs. Optionally, red blood cells are lysed prior to treatment, nanoparticle concentration increased, their size altered, or incorporating multiple treatment steps.

EXAMPLE 3

Figure 2:
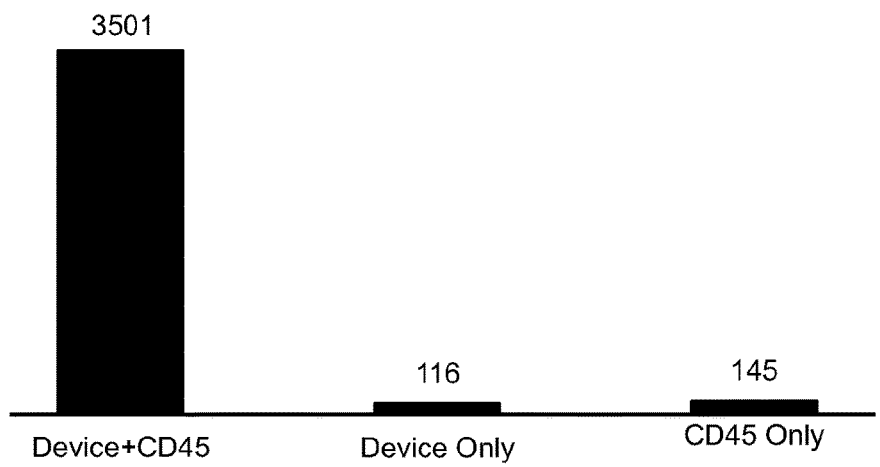
FIG. 2 is a bar graph showing that combining size selective delivery of the microfluidic platform with antibody staining for CD45 produces a sample enrichment factor over an order of magnitude better than either technique independently.
Figure 3A:
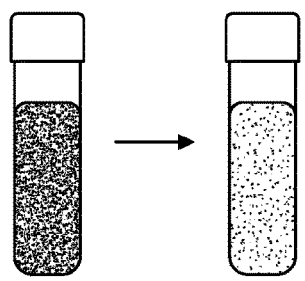
FIG. 3A is a schematic diagram of cell labeling. Red blood cells (RBCs) were depleted from whole blood by RBC lysis using standard erythrocyte lysis reagents such as eBioscience RBC lysis buffer (Cat. No. 00-4333). The resulting suspension flowed through the constriction channel microfluidics device incubated with a fluorescent dye (and optionally other compounds). The suspension was then labeled for CD45 and processed on a fluorescence-activated cell sorter (FACS) machine to collect the non-CD45+ cells that have been labeled with the fluorescent dye.
Figure 3A:
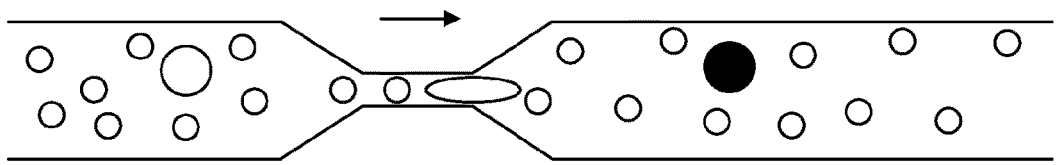
Figure 3A:
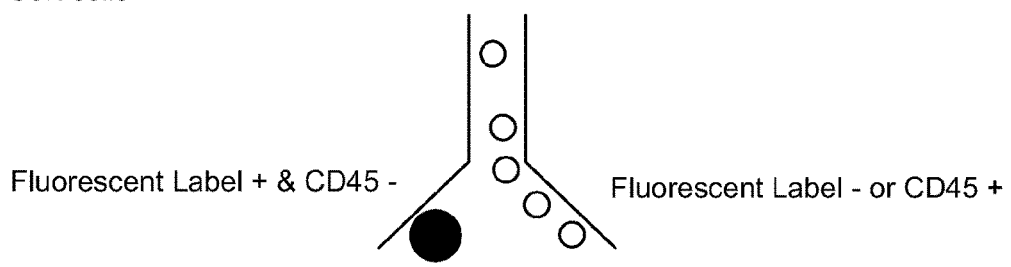
Figure 3B:
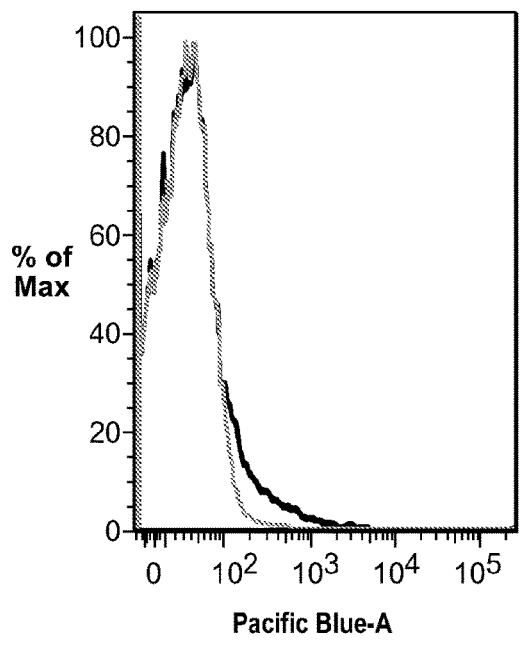
FIG. 3B is a series of flow cytometry plots of cascade blue conjugated 3 kDa dextran delivered by CellSqueeze devices to PBMCs (30-6 chip at 50 psi), HT-29 (30-6 chip at 50 psi), SK-MEL-5 (10-7 chip at 50 psi), and PANC-1(10-7 chip at 50 psi).
Figure 3B:
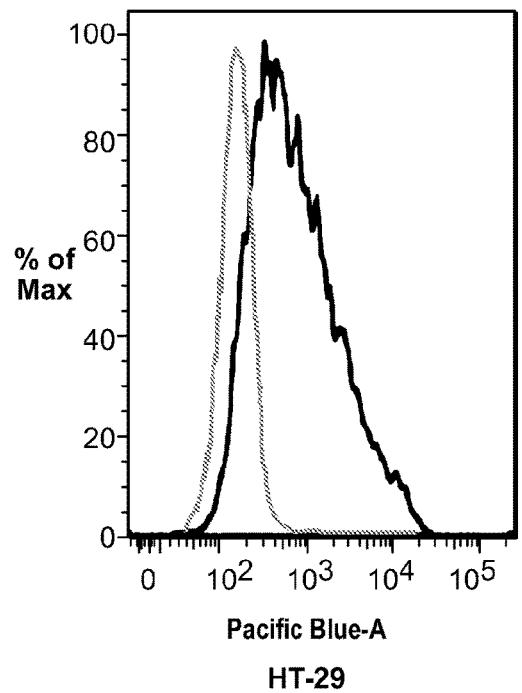
Figure 3B:
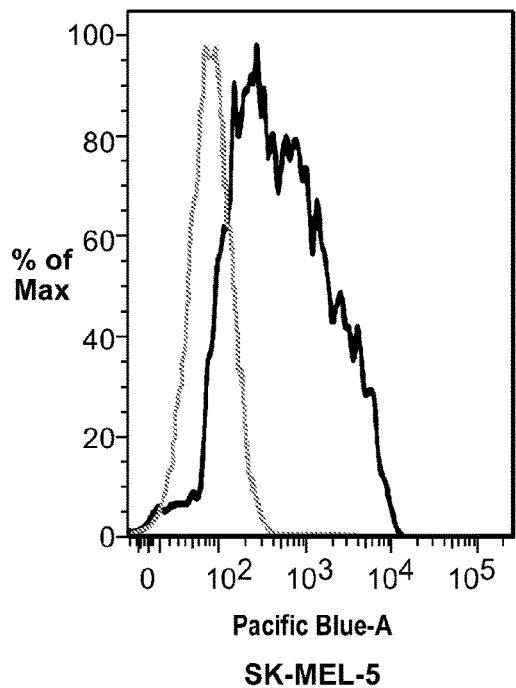
Figure 3B:
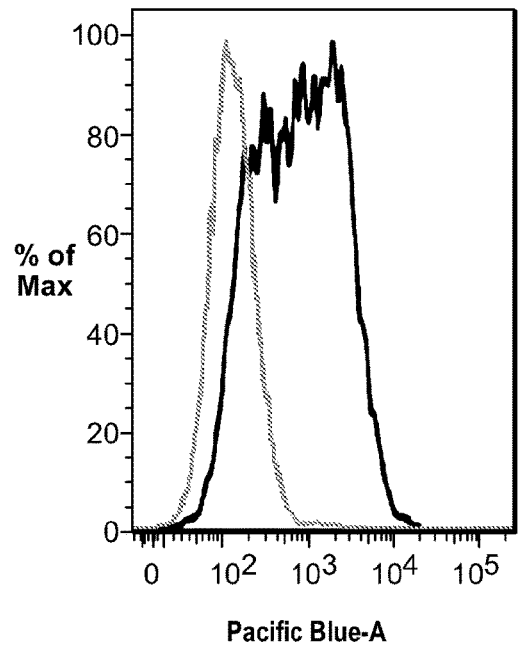
Figure 3C:
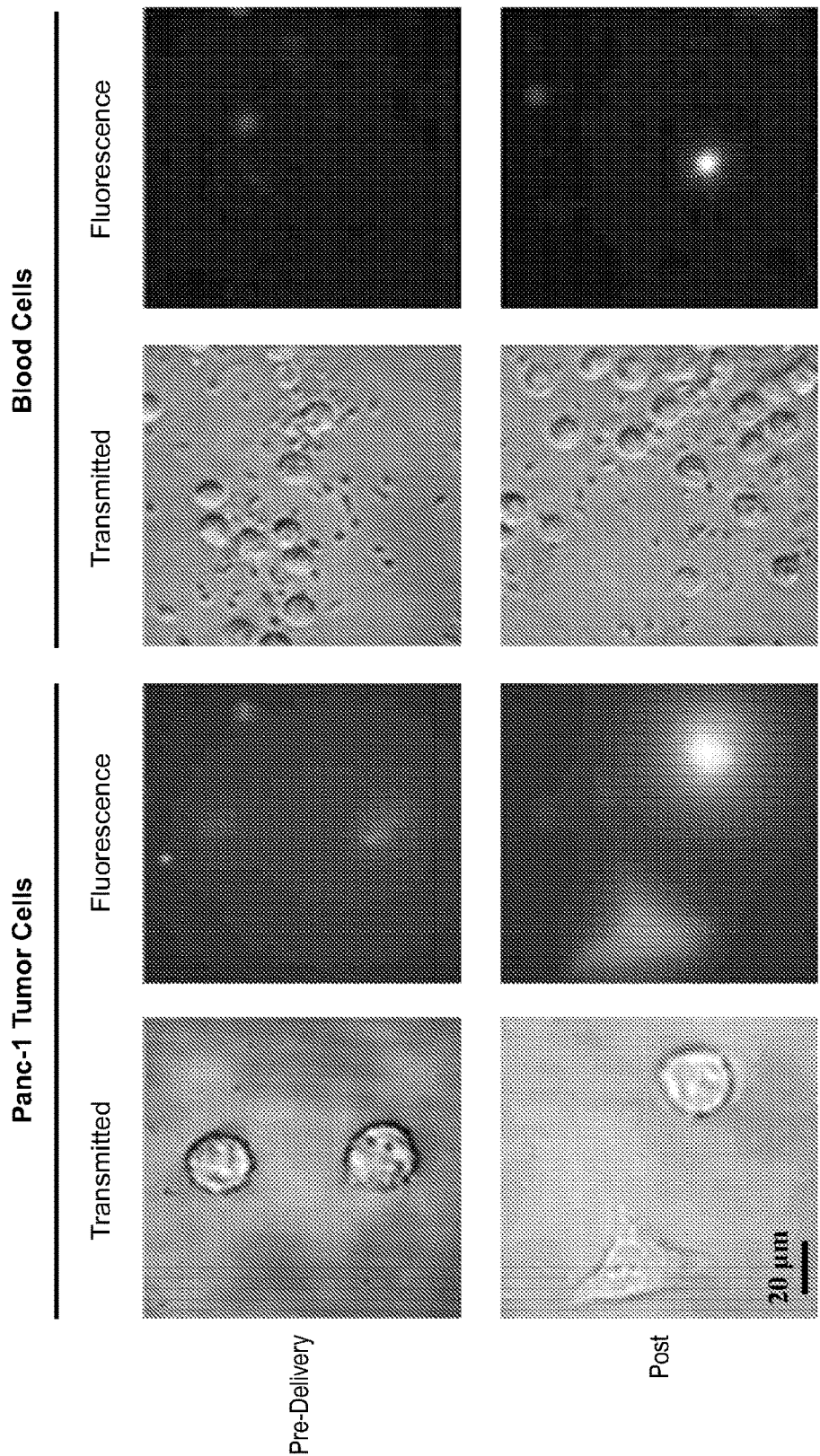
FIG. 3C is a series of transmitted light and fluorescence micrographs of Panc-1 tumor cells and blood cells before and after passing through the constriction channel. The pre-delivery cells are incubated in the presence of dye to correct for background endocytosis. The post-delivery images were taken 24 h after delivery to demonstrate retention of dye and ability of the cells to adhere and grow following delivery. Although large blood cells can also get labeled in the process, these data demonstrate selective labeling of tumor cells.
Figure 4:
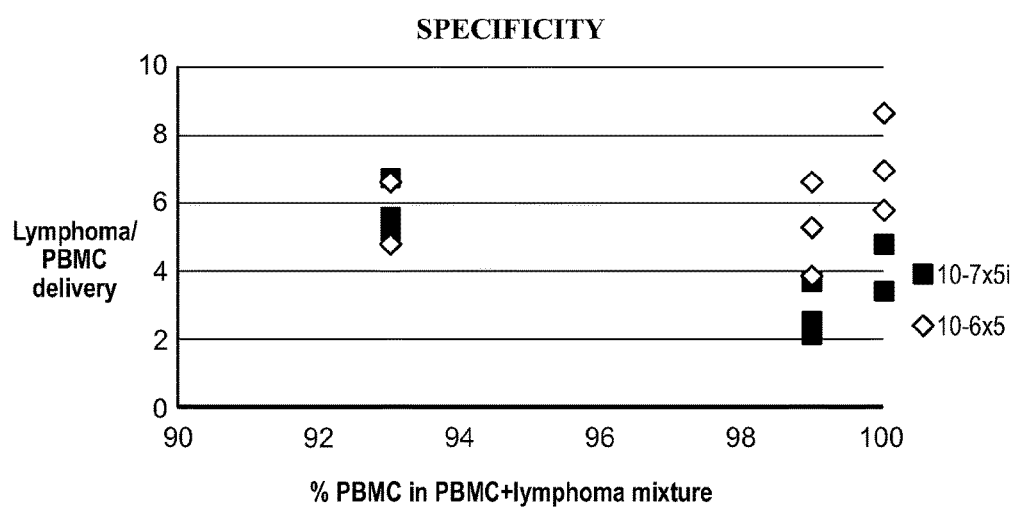
FIG. 4 is a plot of PBMC delivery versus percent PBMC in PBMC and lymphoma mixture showing selective delivery of dyes to lymphoma cells vs. healthy PBMCs. Even when the suspension is 99.9% healthy PBMCs by number, in some implementations up to 8 times specificity in delivery can be acheived. In other implementations, greater specificity can be achieved.
Figure 5A:
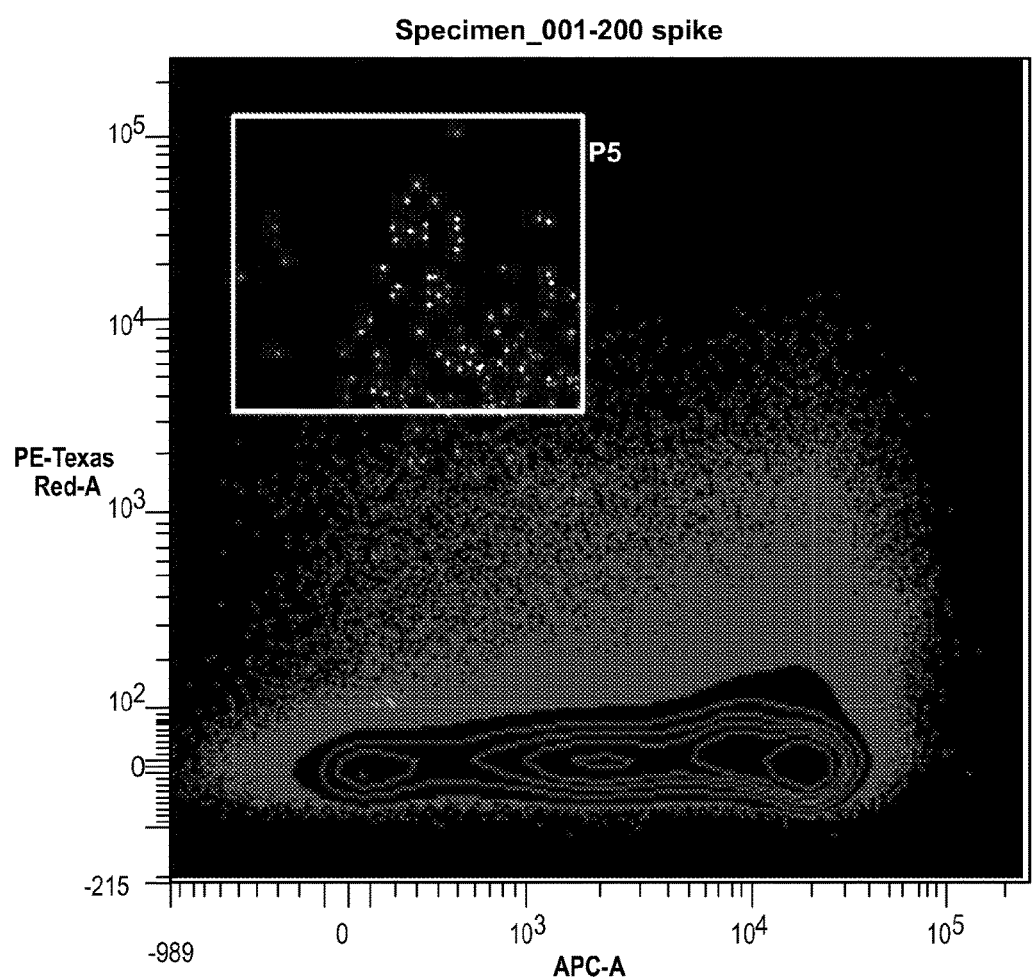
FIG. 5A is a FACS plot of tetramethylrhodamine dextran-labeled Panc-1-GFP cells spiked into whole blood (40 cells/ml) and processed with a CD45 counter stain (APC).
Figure 5B:
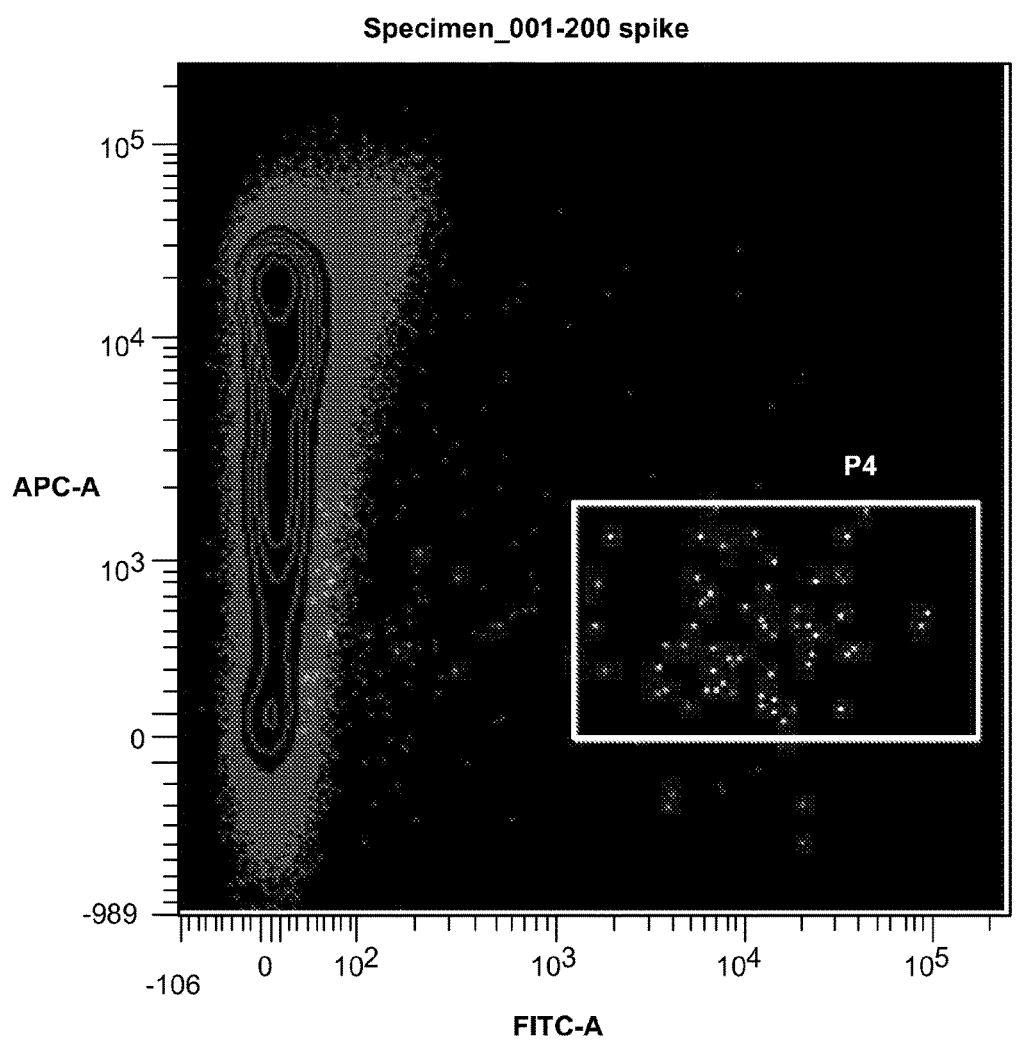
FIG. 5B is a FACS plot of GFP versus CD45, demonstrating how PANC-1 GFP tagging could be verified independently based on GFP fluorescence. The P5 gate would be used as a basis for sorting candidate CTCs, P4 is used to verify the identity of PANC-1 GFP cells. Green dots are accurate hits (P4 & P5), red dots are false positives (P5 only), blue dots are misses (P4 only).
Figure 5C:
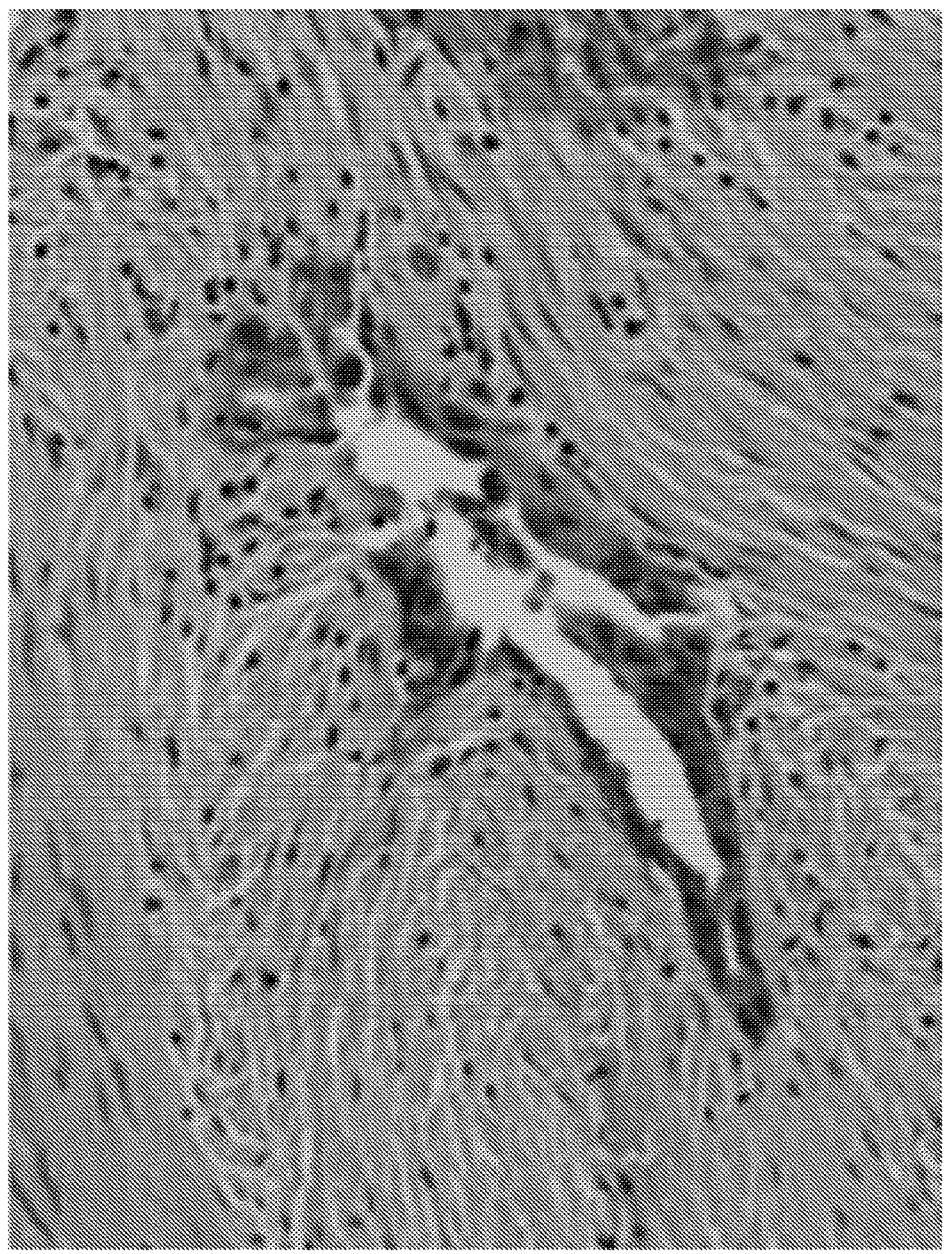
FIG. 5C is an image of histopathology of HTB1760's primary tumor confirms pancreatic ductal adenocarcinoma.

A combined immunological and morphologic-based method is carried out as follows. After cell size-based processing by the device, cells are treated with an antibody or other tumor cell specific ligand such as fluorescently labeled anti-CD45 antibodies. The sensitivity and specificity of three different separation approaches were compared:: 1) device only 2) anti-CD45 antibody only 3) device+anti-CD45 antibody. Morphologic tagging (device)+immunological tagging (e.g., anti-CD45 antibodies) was found to show superior sensitivity (and specificity) relative to either of the individual techniques (FIG. 2). For example, a 2-5× increase in sensitivity and/or a 2-5× increase in specificity relative to anti-CD45 antibodies alone is observed. Enrichment factor of over an order of magnitude was observed (FIG. 2).

EXAMPLE 4

In one example, the devices are fabricated out of silicon and glass. Alternatively, the device is fabricated using a polymer such as silicone, PDMS, polycarbonate, acrylic, polypropylene, polystyrene. Either device is sterilized (heat or gamma radiation) and disposable. Performance of the devices is validated for various cell types using materials and parameters. For example, performance at a range of flow speeds (100 mm/s-10,000 mm/s) using PEG coated quantum dots (ranging from 10-50 nm in size) is used to determine if the delivery efficiency of nanoparticles and cell viability. Exemplary device are described in PCT/US2012/060646, hereby incorporated by reference.

Advantages

When compared to existing approaches this method has the following advantages. Relative to antibody-based methods, this approach provides a non-biased isolation procedure that is generalizable to most cancer types and is independent of any particular cell surface marker. The device and method accomplishes the identification of CTCs that could not be isolated by existing markers and thus, has significant diagnostic and prognostic implications.

Relative to existing size-based isolation methods, the device and methods described herein provide far higher throughput and are tunable by varying "W" (FIG. 1) to capture specific CTC size ranges. For example, a 6 µm width constriction is suitable for the capture of colon cancer cells whereas a 7 µm, and 8 µm width are suitable for the capture of pancreatic cancer and melanoma cells respectively. Moreover, unlike existing technologies, this system is combined with antibody-based technologies to enhance isolation sensitivity and/or enable multi-parametric isolation of subsets of CTCs (for example by isolating CTCs of a certain size+surface marker).

By enabling the effective, robust isolation of CTCs from a range of cancer types this technology would be a valuable platform in the fight against cancer. The prognostic and diagnostic potential of this technology could enable the identification of new genes that are critical to cancer progression and thus enable the development of novel therapeutics. It may also provide a more accurate prediction of patient life-expectancy and treatment efficacy.

The CTC isolation methods described herein combines immunological and size-based isolation to yield a high enrichment factor/recovery rate and adjustable bias (marker specific vs. size specific).

Although a few variations have been described in detail above, other modifications are possible. For example, the implementations described above can be directed to various combinations and subcombinations of the disclosed features and/or combinations and subcombinations of several further features disclosed above. In addition, the logic flows described herein do not require the particular order described, or sequential order, to achieve desirable results. Other embodiments may be within the scope of the following claims.

The invention claimed is:

1. A method for delivering a compound into a cell based on a physical property of said cell comprising:
providing a cell suspension comprising a first group of cells and a second group of cells, wherein the first group of cells comprises tumor cells, and the second group of cells comprises whole blood cells;
passing said cell suspension through and out of a microfluidic channel that includes a constriction, said constriction comprising a width from 4-10 µm, a length of 1-100 µm, and 1-10 constrictions in series, to deliver a compound to the first group of cells to a greater extent than the second group of cells, wherein passage through the constriction disrupts the cell membranes of the first group of cells such that the compound is delivered into the first group of cells to a greater extent than the second group of cells in the cell suspension that passes through and out of the microfluidic channel; and
contacting said cell suspension with the compound.

2. The method of claim 1, wherein said cell suspension comprises peripheral blood cells.

3. The method of claim 1, wherein said second group of cells is an erythrocyte-depleted population of peripheral blood cells.

4. The method of claim 1, wherein said compound has a molecular mass of 0.5 kDa to 5 MDa.

5. The method of claim 1, wherein said compound has a molecular mass of 3 kDa to 10 kDa.

6. The method of claim 1, wherein said compound comprises one or more of a detectable marker, an active biomolecule, and a toxin.

7. The method of claim 1, wherein said compound comprises a detectable marker.

8. The method of claim 1, wherein second group of cells is whole blood cells are obtained from a subject at risk of or diagnosed as comprising a tumor.

9. The method of claim 8, wherein said tumor is melanoma, colon, prostate, lung, pancreatic, breast, liver, brain, or blood cancer.

10. The method of claim 1, wherein the speed of the cells traversing the constriction ranges from 10mm/s to 10m/s.

11. The method of claim 1, further comprising applying a pressure to the cell suspension to drive the cells suspension through the constriction of the microfluidic channel.

12. The method of claim 1, wherein said cell suspension comprises the compound or wherein said method further comprises a step of incubating said cell suspension in a solution containing the compound for a predetermined time after it passes through the constriction.

13. The method of claim 12, wherein the compound comprises a dye, a protein, or a nucleic acid.

14. The method of claim 12, wherein the compound comprises a magnetic particle, a fluorescent particle, a fluorescent dye, a fluorescent protein, nucleic acid encoding a fluorescent protein, luciferase, or a compound that induces cell death.

15. The method of claim 7, further comprising sorting the cells in the cell suspension based on uptake of the detectable marker, thereby isolating the first group of cells.

16. The method of claim 7, further comprising tagging the cells in the cell suspension with an antibody and sorting the cells in the cell suspension based on uptake of the detectable marker and/or antibody tagging, thereby isolating the first group of cells.

17. The method of claim 16, wherein the antibody binds a target on the first group of cells, and the cells are sorted by presence of the detectable marker and presence of the antibody tag, and wherein the antibody is a blood cell selective antibody.

18. The method of claim 16, wherein the antibody binds a target on the second group of cells, and cells are sorted by presence of the detectable marker and absence of the antibody tag, and wherein the antibody is a blood cell selective antibody.

19. The method of claim 1, wherein at least 10% more of the compound is delivered into the first group of calls compared to the second group of cells.

* * * * *